(12) United States Patent
Hong

(10) Patent No.: US 6,975,961 B1
(45) Date of Patent: Dec. 13, 2005

(54) SYSTEM HAVING DIGITAL WEIGHING SCALE DEVICE AND METHOD FOR OUTPUTTING DIET INFORMATION TRANSMITTED THROUGH INTERNET NETWORK

(75) Inventor: Sung Sun Hong, Songpa-Gu (KR)

(73) Assignee: AIIA Communication Corp., Seoul (KR)

( * ) Notice: Subject to any disclaimer, the term of this patent is extended or adjusted under 35 U.S.C. 154(b) by 124 days.

(21) Appl. No.: 10/297,977

(22) PCT Filed: Nov. 2, 2000

(86) PCT No.: PCT/KR00/01252

§ 371 (c)(1),
(2), (4) Date: Dec. 12, 2002

(87) PCT Pub. No.: WO01/97154

PCT Pub. Date: Dec. 20, 2001

(30) Foreign Application Priority Data

Jun. 12, 2000 (KR) ............... 2000/32061
Nov. 1, 2000 (KR) ............... 2000/64609

(51) Int. Cl.$^7$ .............. G01G 11/00; G01G 19/40
(52) U.S. Cl. ................... 702/173; 177/25.16
(58) Field of Search ............ 702/173; 177/25.16; 600/300

(56) References Cited

U.S. PATENT DOCUMENTS 4,773,492 A * 9/1988 Ruzumna ............... 177/25.19
6,497,657 B2 * 12/2002 Nunome ................ 600/300
6,538,215 B2 * 3/2003 Montagnino et al. .... 177/25.16
6,602,191 B2 * 8/2003 Quy ...................... 600/300
6,612,984 B1 * 9/2003 Kerr, II .................. 600/300
6,735,479 B2 * 5/2004 Fabian et al. ............ 607/60

FOREIGN PATENT DOCUMENTS

| JP | 07-74841 | 3/1995 |
| JP | 11-85650 | 3/1999 |
| JP | 11-136391 | 5/1999 |
| JP | 11-219391 | 8/1999 |

* cited by examiner

*Primary Examiner*—John Barlow
*Assistant Examiner*—Toan M. Le
(74) *Attorney, Agent, or Firm*—Jordan and Hamburg LLP (57) ABSTRACT

A system includes the Internet network; a digital weighing scale device, coupled to the Internet network, for weighing a current user body to detect a current weight value and outputting diet information; and a server computer, coupled to the Internet network, for providing the diet information corresponding to the current weight value to the digital weighing scale device. The digital weighing scale device has a liquid crystal display (LCD) and a printer. The system further includes a client computer. The server computer has a World-Wide Web (Web) site, which is made up of at least one Web page. A user at the digital weighing scale device can input user-input information into the server computer, wherein the user-input information includes a user identity, a user sex, a user height value, user waist and hip circumference values, a target time period and a target weight value. Alternatively, the user at the client computer can input the user-input information into the Web page.

125 Claims, 7 Drawing Sheets

SYSTEM HAVING DIGITAL WEIGHING SCALE DEVICE AND METHOD FOR OUTPUTTING DIET INFORMATION TRANSMITTED THROUGH INTERNET NETWORK

TECHNICAL FIELD

The present invention relates to a digital weighing scale; and, more particularly, to a system and method for outputting diet information transmitted through an Internet network, wherein the system has a digital weighing scale device including a liquid crystal display (LCD) and a printer.

BACKGROUND ART

Generally, a conventional digital weighing scale includes a digital data processing apparatus for computing and displaying a quantity representative of or proportional to weight on the digital weighing scale in accordance with a computational algorithm which is at least partly determined by variable parameters selected by a user of the digital weighing scale. However, there is a problem that the conventional digital weighing scale can not display or print information transmitted through an Internet network.

DISCLOSURE OF INVENTION

It is, therefore, an object of the present invention to provide a system having a digital weighing scale device and method, which can display and print diet information transmitted through an Internet network.

It is, therefore, another object of the present invention to provide a computer-readable medium storing program instructions, the program instructions disposed on a computer to perform a method for displaying and printing diet information transmitted through an Internet network.

In accordance with an aspect of the present invention, there is provided a system for outputting diet information, comprising: a common communication line; a weighing scale device, coupled to said common communication line, for weighing a current user body to detect a current weight value; and outputting the diet information; and an information provision means, coupled to said common communication line, for providing the diet information corresponding to the current weight value to said weighing scale device.

In accordance with another aspect of the present invention, there is provided a method for outputting diet information, comprising the steps of: a) weighing a current user body to detect a current weight value; b) providing the diet information corresponding to the current weight value from a sever computer to a weighing scale device; and c) outputting the diet information.

In accordance with further another aspect of the present invention, there is provided a computer-readable medium storing program instructions, the program instructions disposed on a computer to perform a method for outputting diet information, the method comprising the steps of: a) weighing a current user body to detect a current weight value; b) providing the diet information corresponding to the current weight value from a sever computer to a weighing scale device; and c) outputting the diet information.

BRIEF DESCRIPTION OF THE DRAWINGS

The above and other objects and features of the instant invention will become apparent from the following description of preferred embodiments taken in conjunction with the accompanying drawings, in which.

BEST MODE FOR CARRYING OUT THE INVENTION

Figure 1:
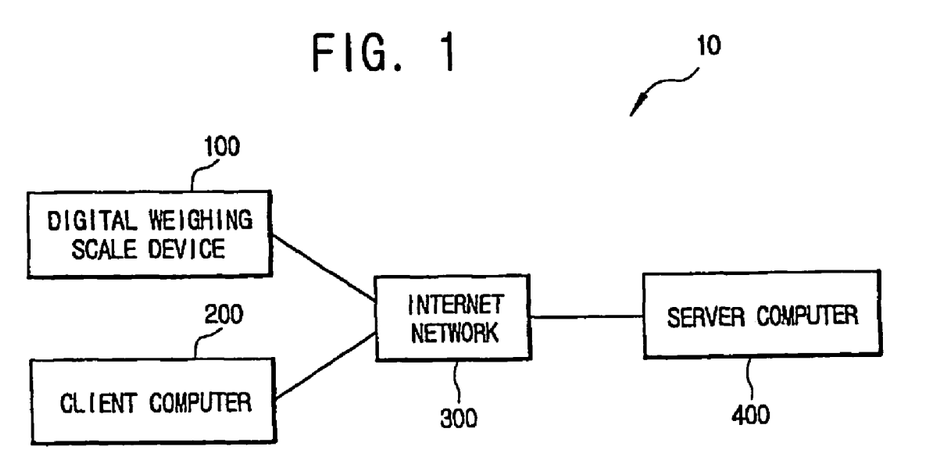
FIG. 1 is an exemplary block diagram illustrating a system having a digital weighing scale device in accordance with the present invention.

Referring to FIG. 1, there is shown an exemplary block diagram illustrating a system having a digital weighing scale device in accordance with the present invention. As shown, a system 10 includes a digital weighing scale device 100, a client computer 200, an Internet network 300 and a server computer 400. The digital weighing scale device 100, coupled to the Internet network 300, weighs a current user body to detect a current weight value. The server computer 400, coupled to the Internet network 300, provides the diet information corresponding to the current weight value to the digital weighing scale device 100. The digital weighing scale device 100 displays or prints the diet information outputted from the server computer 400. The diet information includes a weight variation value, today diet list and recommended physical exercise information. The weight variation value includes a weight increment and a weight decrement. Today diet list includes breakfast, lunch and supper diet (health) foods.

Further, the client computer 200 can be coupled to the Internet network 300. The client computer 200 communicates with the server computer 400 via the Internet network 300, thereby transmitting user-input information to the server computer 400. The user-input information includes a user identity (ID), a user sex, a user weight value, user waist and hip circumference values, a target time period and a target weight value. Alternatively, a user at the client computer 200 can input enjoyable physical exercise information into the server computer 400 through the Internet network 300. The recommended physical exercise information can be based on the enjoyable physical exercise information, e.g., sports.

Figure 2:
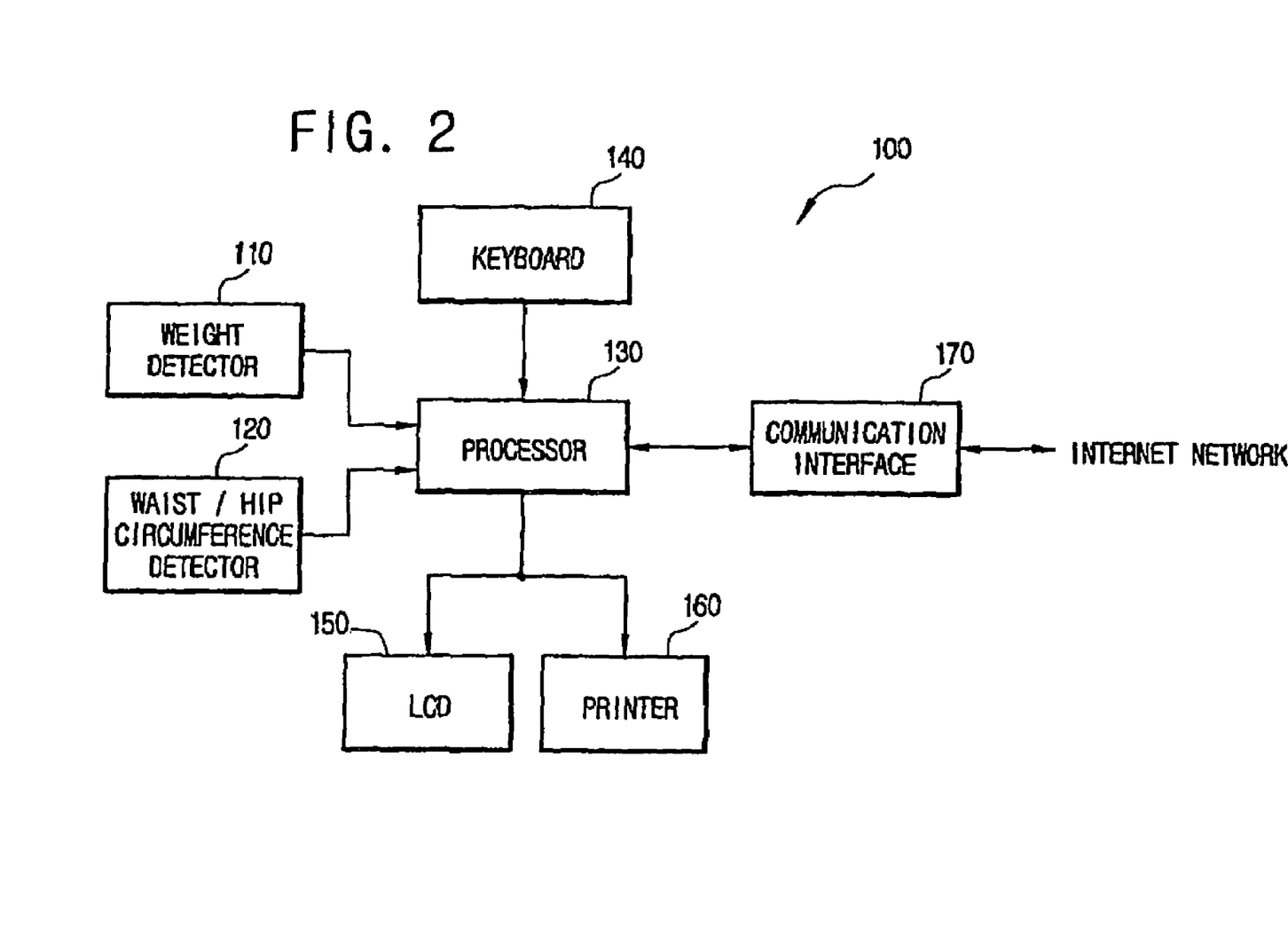
FIG. 2 is an exemplary block diagram describing a digital weighing scale device shown in FIG. 1.

Referring to FIG. 2, there is shown an exemplary block diagram describing a digital weighing scale device shown in FIG. 1. As shown, the digital weighing scale device 100 includes a weight detector 110, a waist/hip circumference detector 120, a processor 130, a keyboard 140, a liquid crystal display (LCD) 150, a printer 160 and a communication interface 170. The weight detector 110 is coupled to a weighing pad (not shown). The weighing pad weighs a current user body. The weight detector 110 detects a current weight value from the current user body weighed by the weighing pad. The waist/hip circumference detector 120 is coupled to a measuring rope (not shown). Similarly, the measuring rope measures user waist and hip circumferences. The waist/hip circumference detector 120 detects current waist and hip circumference values from the waist and hip circumferences measured by the measuring rope. At this time, the processor 130 processes the current weight value and the current waist and hip circumference values. The communication interface 170 sends the current weight value and the current waist and hip circumference values processed by the processor 130.

The keyboard 140 representing an input device receives user-input information from a user, wherein the keyboard 140 has a plurality of keys. At this time, the user inputs the user-input information through the keys, wherein the user-input information includes a user ID, a user sex, a user height value, user waist and hip circumference values, a target time period and a target weight value. The target time period is defined as a predetermined time period necessary to loss weight, wherein the target time period is determined by the user.

The LCD 150 representing an output device displays processed information, e.g., processed diet information, from the server computer 400. The printer 160 representing another output device prints the processed information, e.g., the processed diet information, in the form of written data. The communication interface 170 transmits the user-input information, the current weight value, and the current waist and hip circumference values to the server computer 400 over the Internet network 300. Further, the communication interface 170 receives the diet information corresponding to the user-input information from the server computer 400 over the Internet network 300.

Figure 3:
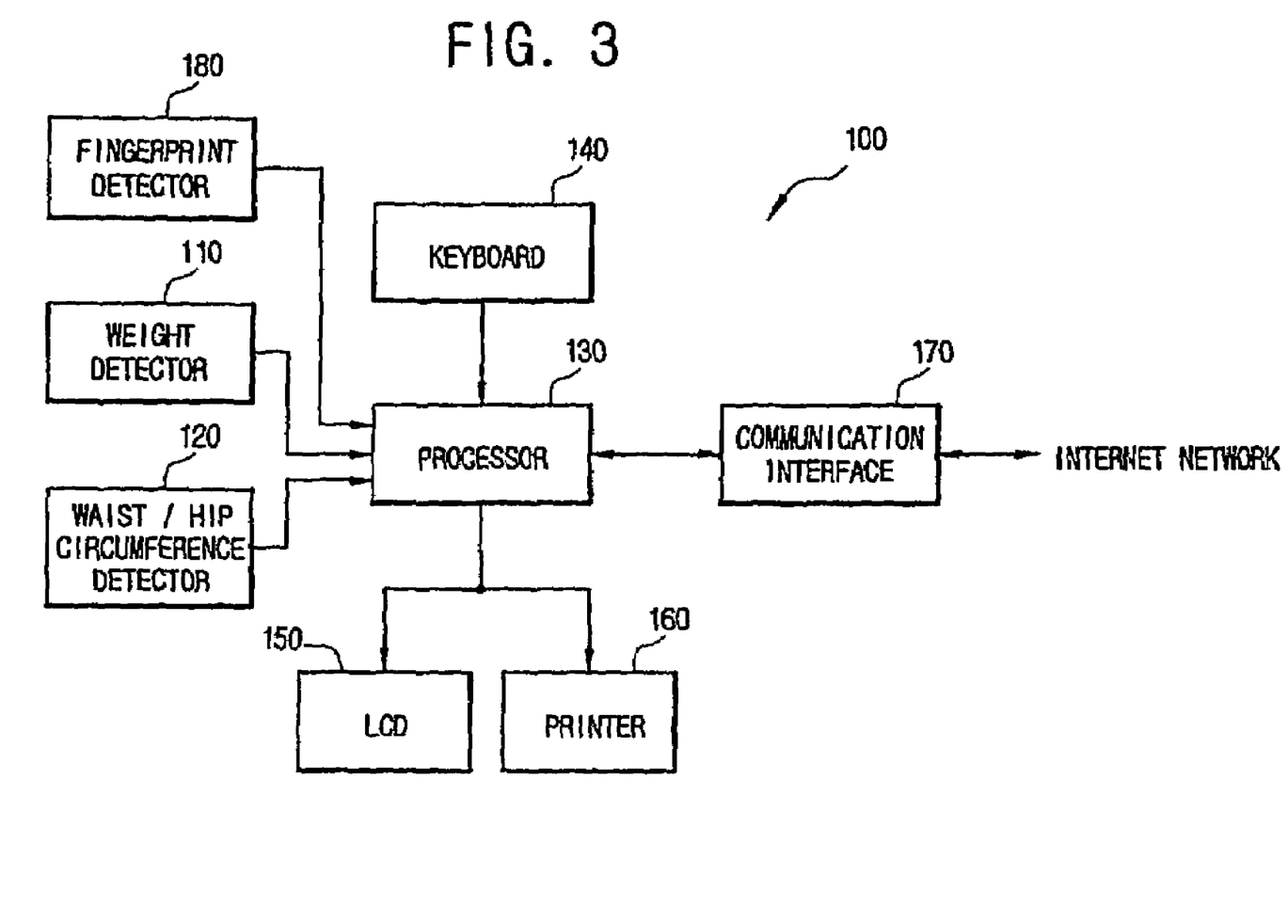
FIG. 3 is another exemplary block diagram describing a digital weighing scale device shown in FIG. 1.

Referring to FIG. 3, there is shown another exemplary block diagram describing a digital weighing scale device shown in FIG. 1. As compared to a structure of the digital weighing scale device 100 shown in FIG. 2, a structure of the digital weighing scale device 100 shown in FIG. 3 further includes a fingerprint detector 180. The fingerprint detector 180 detects a user fingerprint in order to identify the user. Accordingly, the digital weighing scale device 100 can identify the user from the user fingerprint detected by the fingerprint detector 180.

Figure 4:
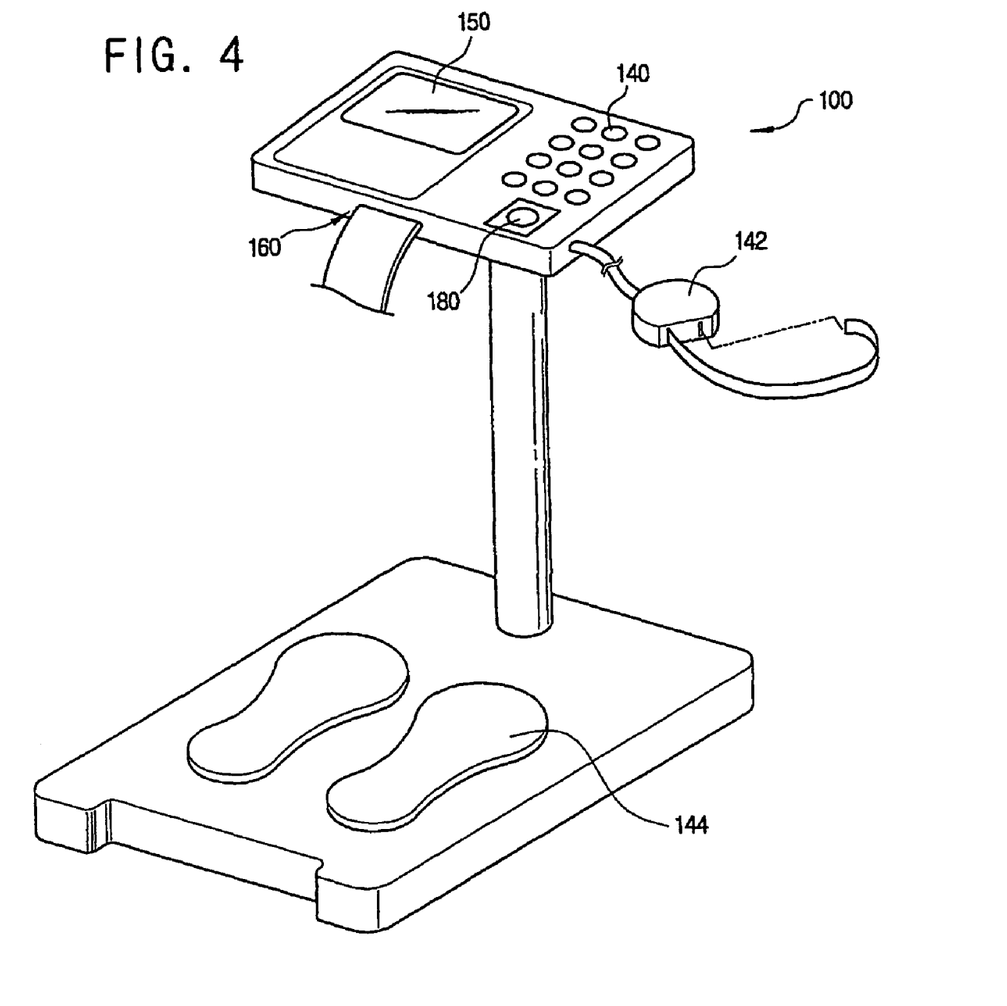
FIG. 4 is an exemplary perspective view depicting a digital weighing scale device shown in FIG. 1.

Referring to FIG. 4, there is shown an exemplary perspective view depicting a digital weighing scale device shown in FIG. 1. As shown, the digital weighing scale device 100 includes a weighing pad 144 and a measuring rope 142. The weighing pad 144 weighs a current user body. The measuring rope 142 measures user waist and hip circumferences. The keyboard 140, the LCD 150 and the printer 160 contained in the digital weighing scale 100 can be implemented as a built-in type. The fingerprint detector 180 is located beneath the keyboard 140.

Figure 5:
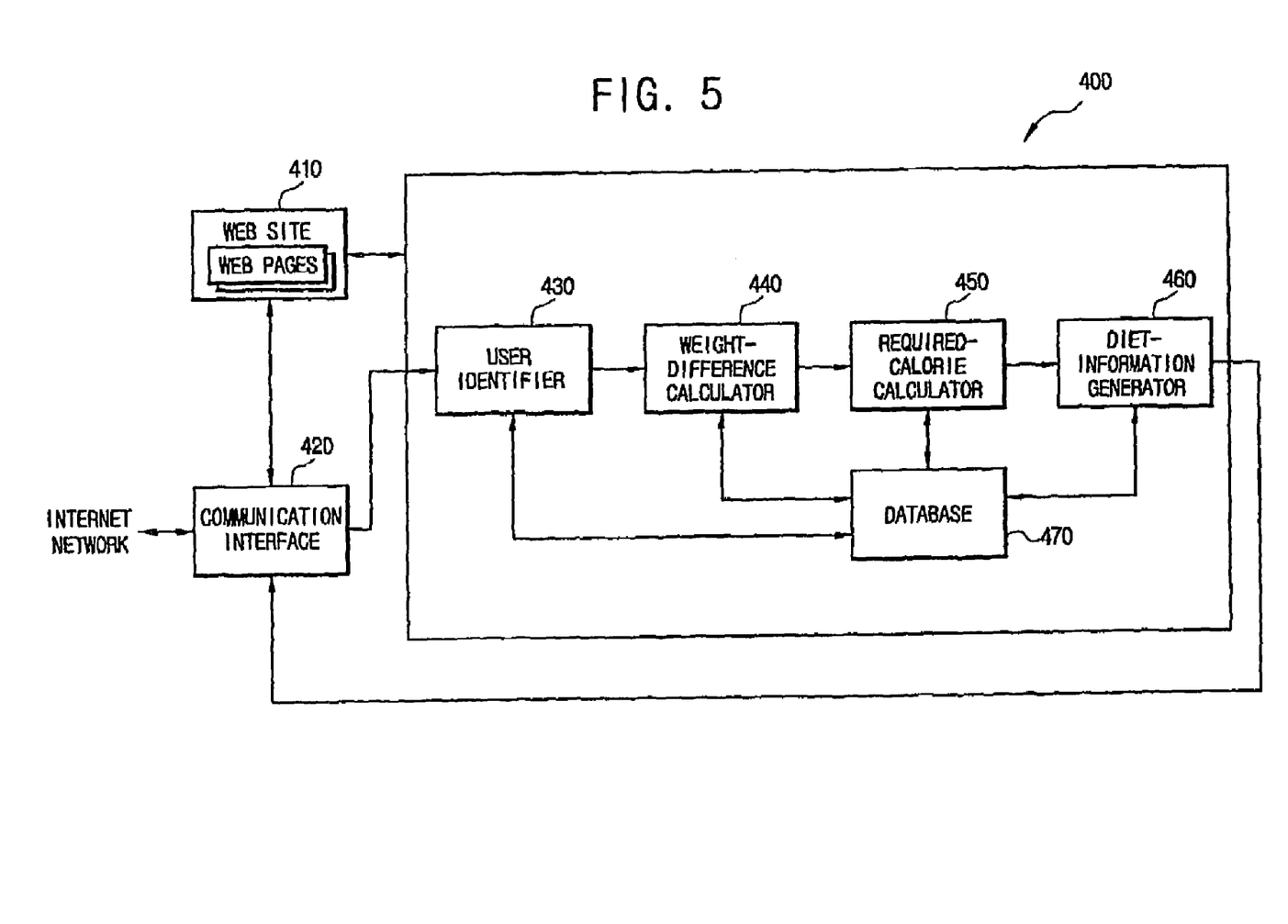
FIG. 5 is an exemplary block diagram showing a server computer shown in FIG. 1.
Figure 6:
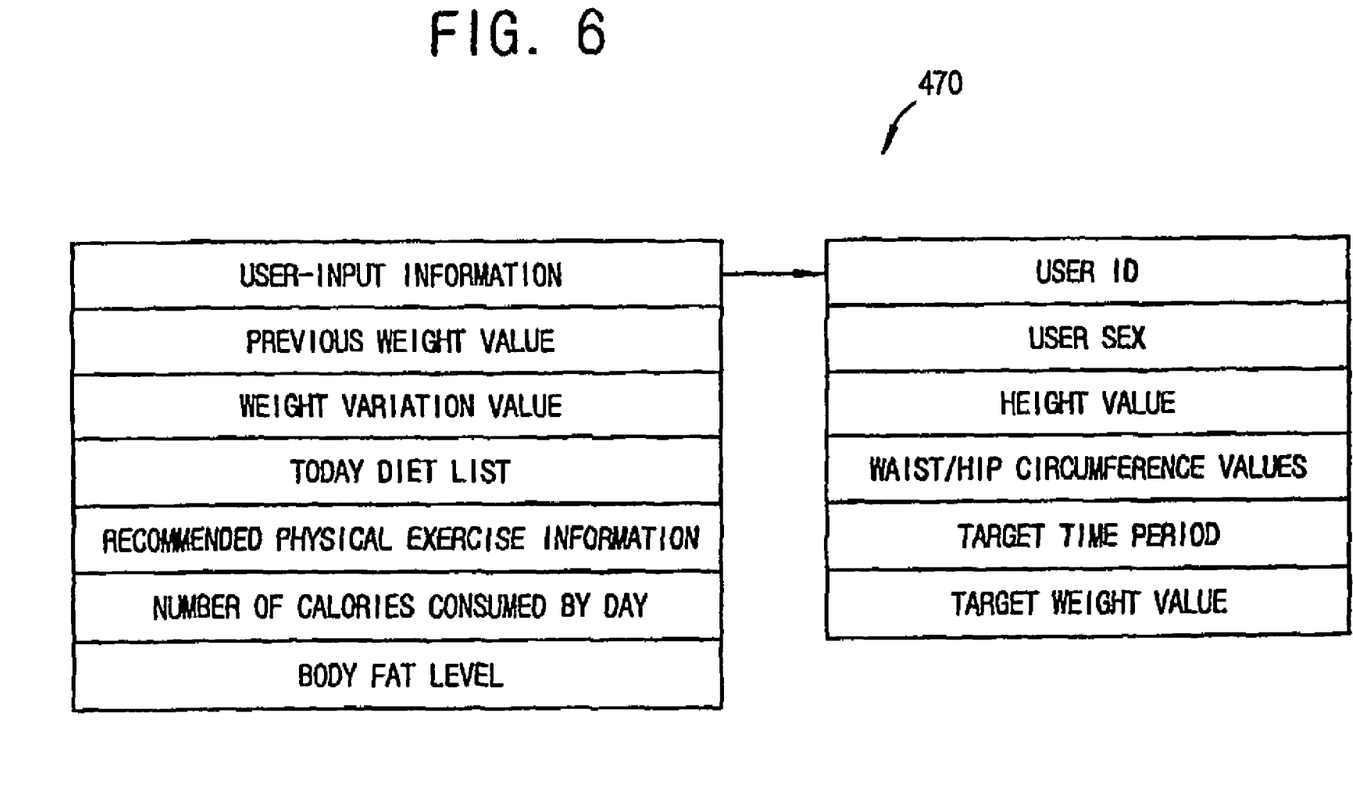
FIG. 6 illustrates an exemplary configuration of a database shown in FIG. 5.

Referring to FIG. 5, there is shown an exemplary block diagram showing a server computer shown in FIG. 1. As shown, the server computer 400 includes a World-Wide Web (Web) site 410, a communication interface 420, a user identifier 430, a weight-difference calculator 440, a required-calorie calculator 450, a diet-information generator 460 and a database 470. The Web site 410 includes at least one Web page, wherein the Web page has user-input information received via the communication interface 420 from the client computer 200. A user at the client computer 200 can register the user ID to the server computer 400 via the Web page. Similarly, the user at the digital weighing scale device 100 can register the user ID to the server computer 400. The communication interface 420 receives the user-input information and a current weight value of the user from the digital weighing scale device 100. The user identifier 430 coupled to the database 470 identifies a user ID contained in the user-input information by comparing the user ID received from the client computer 200 with a user ID stored in the database 470. Referring to FIG. 6, there is shown an exemplary configuration of a database shown in FIG. 5. The database 470 includes the user-input information, a previous weight value, a weight variation value, today diet list, recommended physical exercise information, the number of calories consumed by the day and a body fat level. The user-input information includes the user ID, a user sex, a user height value, user waist and hip circumference values, a target time period and a target weight value.

If the user ID is identified by the user identifier 430, the weight-difference calculator 440, coupled to the user identifier 430 and the database 470, calculates a difference between the current weight value received from the client computer 200 and the previous weight value stored in the database 470. The required-calorie calculator 450 is coupled to the weight-difference calculator 440 and the database 470. The required-calorie calculator 450 calculates the number of calories required by the day on the basis of the number of calories consumed by the day and the user-body fat level stored in the database 470 as well as the difference calculated by the weight-difference calculator 440. The diet-information generator 460, coupled to the required-calorie calculator 450 and the database 470, is responsive to the number of calories required by the day. The diet-information generator 460 generates the diet information in response to the number of calories required by the day. The diet information includes today diet list, the recommended physical exercise information and weight variation information stored in the database 470. The communication interface 420, coupled to the diet-information generator 460, transmits the diet information to the client computer 200.

Figure 7:
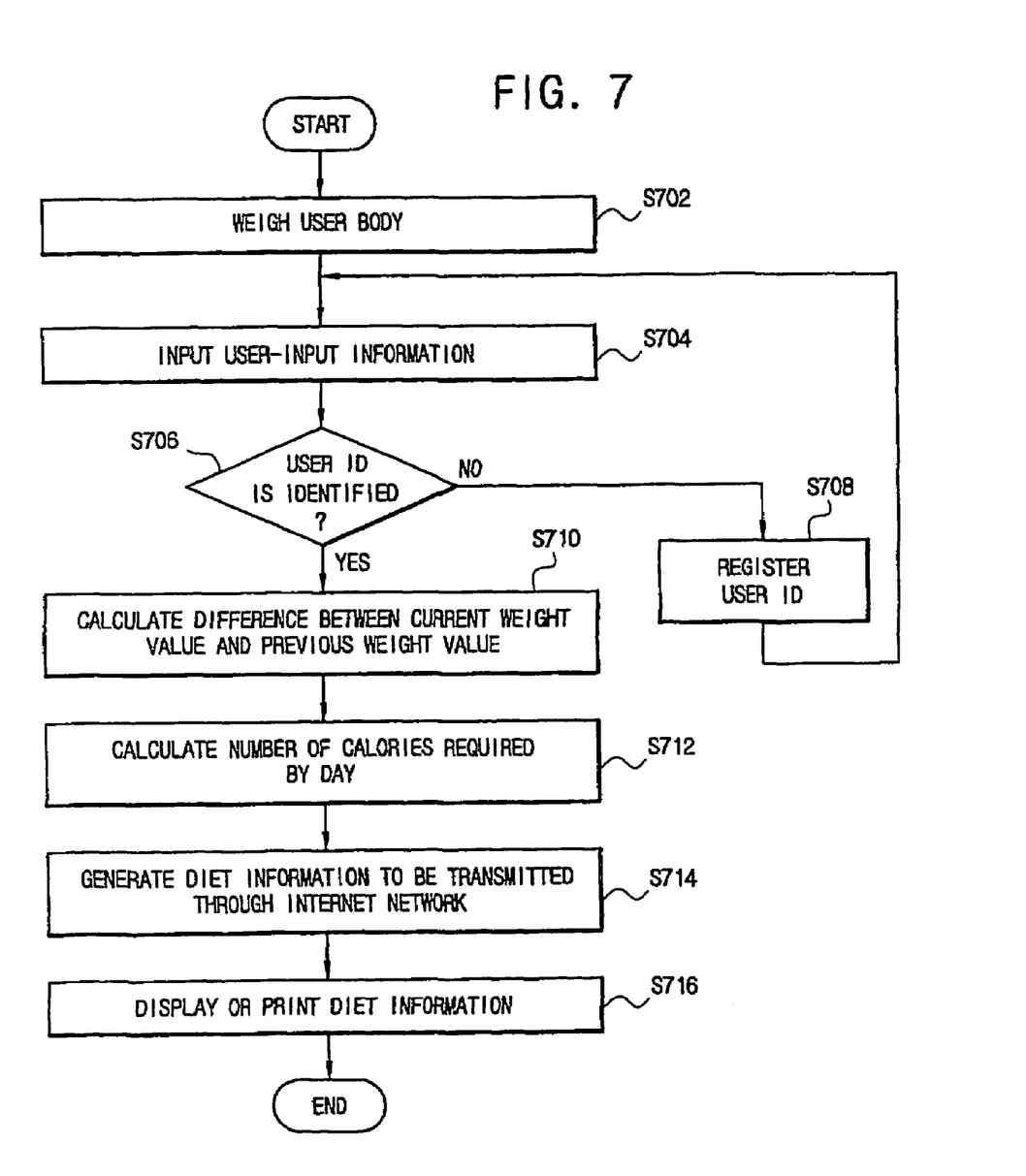
FIG. 7 is an exemplary flowchart illustrating a method for outputting diet information transmitted through an Internet network in accordance with the present invention.

Referring to FIG. 7, there is shown an exemplary flowchart illustrating a method for outputting diet information transmitted through an Internet network in accordance with the present invention. As shown, the weighing pad 144 contained in the digital weighing scale device 100 shown in FIG. 1 weighs, at step S702, a current user body. Thereafter, the weight detector 110 detects a current weight value from the current user body weighed by the weighing pad 144.

Then, a user at the digital weighing scale device 100 inputs, at step S704, user-input information through the keyboard 140 contained in the digital weighing scale device 100. Thereafter, the communication interface 170 contained in the digital weighing scale device 100 transmits the current weight value and the user-input information to the server computer 400. The user-input information includes a user ID, a user sex, a user height value, user waist and hip circumference values, a target time period and a target weight value.

Then, the communication interface 420 contained in the server computer 400 shown in FIG. 1 receives the current weight value and the user-input information from the digital weighing scale device 100. At step 706, the user identifier 430 contained in the server computer 400 determines whether the user ID contained in the user-input information is the same as that stored in the database 470, thereby identifying the user ID received from the digital weighing scale device 100. If the user ID is not identified by the user identifier 430, the user at the digital weighing scale device 100 registers, at step S708, the user ID to the server computer 400.

Otherwise, if the user ID is identified by the user identifier 430, the weight-difference calculator 440 contained in the server computer 400 calculates, at step S710, a difference between the current weight value received from the client computer 200 and a previous weight value stored in the database 470. Thereafter, the required-calorie calculator 450 contained in the server computer 400 calculates, at step S712, the number of calories required by the day on the basis of the number of calories consumed by the day and the user-body fat level stored in the database 470 as well as the difference calculated by the weight-difference calculator 440.

Then, the diet-information generator 460 contained in the server computer 400 generates, at step S714, the diet information in response to the number of calories required by the day. The diet information includes today diet list, the recommended physical exercise information and weight variation information. Thereafter, the communication interface 420 contained in the server computer 400 transmits the diet information to the client computer 200 via the Internet network 300.

Then, the communication interface 170 contained in the client computer 200 receives the diet information via the Internet network 300 from the server computer 400. Thereafter, the processor 130 contained in the client computer 200 processes the diet information. Thereafter, the LCD 150 displays, at step S716, the diet information processed by the processor 130. Alternatively, the printer 160 prints, at step S716, the diet information processed by the processor 130.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A system for outputting diet information, comprising:
a common communicating line;
a weighing scale device, coupled to said common communication line, for weighing a current user body to detect a current weight value; and outputting the diet information;
an information provision means, coupled to said common communication line, for providing the diet information corresponding to the current weight value to said weighing scale device, said information provision means including a storage means for storing a weight variation value, today diet list and recommended physical exercise information; and
said system recommending physical exercise and providing information related to said recommended physical exercise to the current user.

2. The system as recited in claim 1, wherein said weighing scale device includes:
a weighing means for weighing the current user body;
a detection means, coupled to said weighing means, for detecting the current weight value from the current user body weighed by said weighing means;
a process means, coupled to said detection means, for processing the diet information and the current weight value;
a communication interface means, coupled between said common communication line and said processing means for transmitting the current weight value to said information provision means and receiving the diet information from said information provision means; and
an output means, coupled to said process means, for outputting the diet information processed by said process means.

3. The system as recited in claim 2, wherein said weighing scale device further includes:
an input means for inputting user-input information.

4. The system as recited in claim 2, wherein said output means includes:
a display means, coupled to said process means, for displaying the diet information processed by said process means; and
a print means, coupled to said process means, for printing the diet information processed by said process means.

5. The system as recited in claim 4, wherein said display means includes a liquid crystal display (LCD).

6. The system as recited in claim 4, wherein said print means includes a printer.

7. The system as recited in claim 2, said weighing scale device further includes:
a second detection means for detecting a fingerprint of a user to identify the user at said weighing scale device.

8. The system as recited in claim 3, wherein the user-input information includes a user identity, a user sex, a height value, a target time period and a target weight value.

9. The system as recited in claim 8, wherein said information provision means includes:
a communication interface means for receiving the current weight value from said weighing scale device and transmitting the dict information to said weighing scale device;
a user identification means, coupled to said communication interface means, for identifying the user identity contained in the user-input information;
a first calculation means coupled to said user identification means, for calculation a difference between the current weight value and a previous weight value;
a second calculation means, coupled to said first calculation means, for calculating the number of calories required by the day on the basis of the difference, the number of calories consumed by the day and a user-body fat level; and
an information generation means, coupled between said communication interface means and said second calculation means, for generating the diet information in response to the number of calories required by the day.

10. The system as recited in claim 9, wherein said storage means further stores the user-input information, the previous weight value, the number of calories consumed by the day and the user-body fat level.

11. The system as recited in claim 8, wherein said weighing scale device further includes:
a circumference measuring means for measuring waist and hip circumferences; and
a third detection means, coupled to said circumference measuring means, for detecting waist and hip circumference values from the waist and hip circumferences measured by said circumference measuring means.

12. The system as recited in claim 11, wherein the user-input information further includes the waist and hip circumference values.

13. The system as recited in claim 10, wherein the diet information includes the weight variation value, the today diet list and the recommended physical exercise information.

14. The system as recited in claim 10, wherein the weight variation value includes a weight increment and a weight decrement.

15. The system as recited in claim 3, wherein said common communication line is coupled to an Internet network.

16. The system as recited in claim 15, wherein said information provision means includes;
   a server computer coupled to the Internet network, said server computer having a World-Wide Web (Web) site, which is made up of at least one Web page.

17. The system as recited in claim 16, further comprising:
   a client computer coupled to the Web page over the Internet network.

18. The system as recited in claim 17, wherein the Web page contained in the Web site includes the user-input information received from said client computer.

19. The system as recited in claim 3, wherein said input means contained in said weighing scale device includes a keyboard.

20. The system as recited in claim 2, wherein said weighing means contained in said weighing scale device includes a weighing pad.

21. The system as recited in claim 11, wherein said circumference measuring means contained in said weighing scale device includes a measuring rope.

22. A method for outputting diet information, comprising the steps of:
   a) weighing a current user body to detect a current weight value;
   b) providing the diet information corresponding to the current weight value from a server computer to a weighing scale device by employing a database storing a weight variation value, today diet list and recommended physical exercise information; and
   c) outputting the diet information; and
   d) reommending physical exercise and providing information related to said recommended physical exercise to the current user.

23. The method as recited in claim 22, wherein said step a) includes the steps of:
   a1) weighing the current user body;
   a2) detection the current weight value from the current user body weighed; and
   a3) transmitting the current weight value from the weighing scale device to server computer.

24. The method as recited in claim 23, wherein said step a) further includes the step of:
   a4) inputting user-input information.

25. The method as recited in claim 22, wherein said step c) includes the steps of:
   c1) receiving the diet information from the server computer;
   c2) processing the diet information;
   c3) displaying the processed diet information on a liquid crystal display (LCD); and
   c4) printing the processed diet information.

26. The method as recited in claim 24, wherein the user-input information contained in said step a4) includes a user identity, a user sex, a height value, a target time period and a target weight value.

27. The method as recited in claim 26, wherein said step b) includes the steps of:
   receiving the current weight value from the weighing scale device;
   identifying the user identity contained in the user-input information;
   calculation a difference between the current weight value and a previous weight value stored in a database;
   calculating the number of calories required by the day on the basis of the difference, the number of calories consumed by the day and the user-body fat level stored in a database; and
   generating the diet information to the weighing scale device.

28. The method as recited in claim 27, wherein said step b) further includes the step of:
   storing the user-input information, the previous weight value, the weight variation value, the today diet list, the recommended physical exercise information, the number of calories consumed by the day and the body fat level.

29. The method as recited in claim 23, wherein said step a) further includes the step of:
   a5) measuring waist and hip circumferences;
   a6) detecting waist and hip circumference values from the waist and hip circumferences measured; and
   a7) transmitting the waist and hip circumference values from the weighing scale device to the server computer.

30. The method as recited in claim 28, wherein the user-input information contained in said step of storing the user-input information further includes the waist and hip circumference values.

31. The method as recited in claim 28, wherein said diet information includes the weight variation value, the today diet list and the recommended physical exercise information.

32. The method as recited in claim 28, wherein the weight variation value includes a weight increment and a weight decrement.

33. A computer-readable medium storing program instructions, the program instructions disposed on a computer to perform a method for outputting diet information, the method comprising the steps of:
   a) weighing a current user body to detect a current weight value;
   b) providing the diet information corresponding to the current weight value from a server computer to a weighing scale device by employing a database storing a weight variation value, today diet list and recommended physical exercise information;
   c) outputting the diet information; and
   d) recommending physical exercise and providing information related to said recommended physical exercise to the current user.

34. The computer-readable medium as recited in claim 33, wherein said step a) includes the steps of:
   a1) weighing the current user body;
   a2) detecting the current weight value from the weighing scale device to the server computer.

35. The computer-readable medium as recited in claim 34, wherein said step a) further includes the step of;
   a4) inputting user-input information.

36. The computer-readable medium as recited in claim 33, wherein said step c) includes the steps of:
   c1) receiving the diet information from the server computer,
   c2) processing the diet information;
   c3) displaying the processed diet information on a liquid crystal display (LCD); and
   c4) printing the processed diet information.

37. The computer-readable medium as recited in claim 35, wherein the user-input information contained in said step a4) includes a user identity, a user sex, a height value, a target time period and a target weight value.

38. The computer-readable medium as recited in claim 37, wherein said step b) includes the steps of:
   receivinig the current weight value from the weighing scale device;

identifying the user identity contained in the user-input information, calculation a difference between the current weight value and a previous weight value;

calculation the number of calories required by the day on the basis of the difference, the number of calories consumed by the day and a user-body fat level stored in a database;

generation the diet information in response to the number of calories required by the day; and transmitting the diet information to the weighing scale device.

39. The computer-readable medium as recited in claim 38, wherein said step b) further includes the step of:

storing the user-input information, the previous weight value, the weight variation value, the today diet list, the recommended physical exercise information, the number of calories consumed by the day and the body fat level.

40. The computer-readable medium as recited in claim 34, wherein said step a) further includes the steps of:

a5) measuring waist and hip circumferences;

a6) detecting waist and hip circumference value from the waist and hip circumferences measured; and a7) transmitting the waist and hip circumference values from the weighing scale device to the server computer.

41. The computer-readable medium as recited in claim 39, wherein the user-input information contained in said step of storing the user-input information further includes the waist and hip circumference values.

42. The computer-readable medium as recited in claim 39, wherein said diet information includes the weight variation value, the today diet list and the recommended physical exercise information.

43. The computer-readable medium as recited in claim 39, wherein the weight variation value contained in the diet information includes a weight increment and a weight decrement.

44. A system for outputting diet information, comprising:

a common communicating line;

a weighing scale device, coupled to said common communication line, for weighing a current user body to detect a current weight value; and outputting the diet information;

an information provision means, coupled to said common communication line, for providing the dict information corresponding to the current weight value to said weighing scale device, said information provision means including a storage means for storing a weight variation value, today diet list and recommended physical exercise information; and said weighting scale including detection means for detecting a fingerprint of a user to identify the user at said weighing scale device.

45. The system as recited in claim 44, includes:

a weighing means for weighing the current user body;

a detection means, coupled to said weighing means, for detecting the current weight value from the current user body weighed by said weighing means;

a process means, coupled to said detection means, for processing the diet information and the current weight value;

a communication interface means, coupled between said common communication line and said processing means for transmitting the current weight value to said information provision means and receiving the diet information from said information provision means; and an output means, coupled to said process means, for outputting the diet information processed by said process means.

46. The system as recited in claim 45, wherein said weighing scale device further includes:

an input means for inputting user-input information.

47. The system as recited in claim 45, wherein said output means includes:

a display means, coupled to said process means, for displaying the diet information processed by said process means; and a print means, coupled to said process means, for printing the diet information processed by said process means.

48. The system as recited in claim 47, wherein said display means includes a liquid crystal display (LCD).

49. The system as recited in claim 47, wherein said print means includes a printer.

50. The system as recited in claim 46, wherein the user-input information includes a user identity, a user sex, a height value, a target time period and a target weight value.

51. The system as recited in claim 50, wherein said information provision means includes:

a communication interface means for receiving the current weight value from said weighing scale device and transmitting the diet information to said weighing scale device;

a user identification means, coupled to said communication interface means, for identifying the user identity contained in the user-input information;

a first calculation means coupled to said user identification means, for calculation a difference between the current weight value and a previous weight value;

a second calculation means, coupled to said first calculation means, for calculating the number of calories required by the day on the basis of the difference, the number of calories consumed by the day and a user-body fat level; and an information generation means, coupled between said communication interface means and said second calculation means, for generating the diet information in response to the number of calories required by the day.

52. The system as recited in claim 51, wherein said storage means further stores the user-input information, the previous weight value, the number of calories consumed by the day and the user-body fat level.

53. The system as recited in claim 50, wherein said weighing scale device further includes:

a circumference measuring means for measuring waist and hip circumferences; and a third detection means, coupled to said circumference measuring means, for detecting waist and hip circumference values from the waist and hip circumferences measured by said circumference measuring means.

54. The system as recited in claim 53, wherein the user-input information further includes the waist and hip circumference values.

55. The system as recited in claim 51, wherein the diet information includes the weight variation value, the today diet list and the recommended physical exercise information.

56. The system as recited in claim 51, wherein the weight variation value includes a weight increment and a weight decrement.

57. The system as recited in claim 46, wherein said common communication line is coupled to an Internet network.

58. The system as recited in claim 57, wherein said information provision means includes:
   a server computer coupled to the Internet network, said server computer having a World-Wide Web (Web) site, which is made up of at least one Web page.

59. The system as recited in claim 58, further comprising:
   a client computer coupled to the Web page over the Internet network.

60. The system as recited in claim 59, wherein the Web page contained in the Web site includes the user-input information received from said client computer.

61. The system as recited in claim 46, wherein said input means contained in said weighing scale device includes a keyboard.

62. The system as recited in claim 45, wherein said weighing means contained in said weighing scale device includes a weighing pad.

63. The system as recited in claim 53, wherein said circumference measuring means contained in said weighing scale device includes a measuring rope.

64. A method for outputting diet information, comprising the steps of:
   a) detecting a fingerprint of a current user to identify the user and weighing the user body to detect a current weight value;
   b) providing the diet information corresponding to the current weight value from a server computer to a weighing scale device by employing a database storing a weight variation value, today diet list and recommended physical exercise information; and
   c) outputting the diet information.

65. The method as recited in claim 64, wherein said step a) includes the steps of:
   a1) weighing the current user body;
   a2) detection the current weight value from the current user body weighed; and
   a3) transmitting the current weight value from the weighing scale device to server computer.

66. The method as recited in claim 65, wherein said step a) further includes the step of:
   a4) inputting user-input information.

67. The method as recited in claim 64, wherein said step c) includes the steps of:
   c1) receiving the diet information from the server computer;
   c2) processing the diet information;
   c3) displaying the processed diet information on a liquid crystal display (LCD); and
   c4) printing the processed diet information.

68. The method as recited in claim 66, wherein the user-input information contained in said step a4) includes a user identity, a user sex, a height value, a target time period and a target weight value.

69. The method as recited in claim 68, wherein said step b) includes the steps of:
   receiving the current weight value from the weighing scale device;
   identifying the user identity contained in the user-input information;
   calculation a difference between the current weight value and a previous weight value stored in a database;
   calculating the number of calories required by the day on the basis of the difference, the number of calories consumed by the day and the user-body fat level stored in a database; and
   generating the diet information to the weighing scale device.

70. The method as recited in claim 69, wherein said step b) further includes the step of:
   storing the user-input information, the previous weight value, the weight variation value, the today diet list, the recommended physical exercise information, the number of calories consumed by the day and the body fat level.

71. The method as recited in claim 65, wherein said step a) further includes the step of:
   a5) measuring waist and hip circumferences;
   a6) detecting waist and hip circumference values from the waist and hip circumferences measured; and
   a7) transmitting the waist and hip circumference values from the weighing scale device to the server computer.

72. The method as recited in claim 70, wherein the user-input information contained in said step of storing the user-input information further includes the waist and hip circumference values.

73. The method as recited in claim 70, wherein said diet information includes the weight variation value, the today diet list and the recommended physical exercise information.

74. The method as recited in claim 70, wherein the weight variation value includes a weight increment and a weight decrement.

75. A computer-readable medium storing program instructions, the program instructions disposed on a computer to perform a method for outputting diet information, the method comprising the steps of:
   a) detecting a fingerprint of a current user to identify the user and weighing the user body to detect a current weight value;
   b) providing the diet information corresponding to the current weight value from a server computer to a weighing scale device by employing a database storing a weight variation value, today diet list and recommended physical exercise information; and
   c) outputting the diet information.

76. The computer-readable medium as recited in claim 75, wherein said step a) includes the steps of:
   a1) weighing the current user body;
   a2) detecting the current weight value from the weighing scale device to the server computer.

77. The computer-readable medium as recited in claim 76, wherein said step a) further includes the step of:
   a4) inputting user-input information.

78. The computer-readable medium as recited in claim 75, wherein said step c) includes the steps of:
   c1) receiving the diet information from the server computer;
   c2) processing the diet information;
   c3) displaying the processed diet information on a liquid crystal display (LCD); and
   c4) printing the processed diet information.

79. The computer-readable medium as recited in claim 77, wherein the user-input information contained in said step a4) includes a user identity, a user sex, a height value, a target time period and a target weight value.

80. The computer-readable medium as recited in claim 79, wherein said step b) includes the steps of:
receiving the current weight value from the weighing scale device;
identifying the user identity contained in the user-input information;
calculation a difference between the current weight value and a previous weight value;
calculation the number of calories required by the day on the basis of the difference, the number of calories consumed by the day and a user-body fat level stored in a database;
generation the diet information in response to the number of calories required by the day; and
transmitting the diet information to the weighing scale device.

81. The computer-readable medium as recited in claim 80, wherein said step b) further includes the step of:
storing the user-input information, the previous weight value, the weight variation value, the today diet list, the recommended physical exercise information, the number of calories consumed by the day and the body fat level.

82. The computer-readable medium as recited in claim 76, wherein said step a) further includes the steps of;
a5) measuring waist and hip circumferences;
a6) detecting waist and hip circumference value from the waist and hip circumferences measured; and
a7) transmitting the waist and hip circumference values from the weighing scale device to the server computer.

83. The computer-readable medium as recited in claim 81, wherein the user-input information contained in said step of storing the user-input information further includes the waist and hip circumference values.

84. The computer-readable medium as recited in claim 81, wherein said diet information includes the weight variation value, the today diet list and the recommended physical exercise information.

85. The computer-readable medium as recited in claim 81, wherein the weight variation value contained in the diet information includes a weight increment and a weight decrement.

86. A system for outputting diet information, comprising:
a common communicating line;
a weighing scale device, coupled to said common communication line, for weighing a current user body to detect a current weight value; and outputting the diet information;
an information provision means, coupled to said common communication line, for providing the diet information corresponding to the current weight value to said weighing scale device, said information provision means including a storage means for storing a weight variation value, today diet list and recommended physical exercise information
said weighing scale device further includes:
a circumference measuring means for measuring waist and hip circumferences; and
a third detection means, coupled to said circumference measuring means, for detecting waist and hip circumference values from the waist and hip circumferences measured by said circumference measuring means.

87. The system as recited in claim 86, wherein said weighing scale device includes:
a weighing means for weighing the current user body;
a detection means, coupled to said weighing means, for detecting the current weight value from the current user body weighed by said weighing means;
a process means, coupled to said detection means, for processing the diet information and the current weight value;
a communication interface means, coupled between said common communication line and said processing means for transmitting the current weight value to said information provision means and receiving the diet information from said information provision means; and
an output means, coupled to said process means, for outputting the diet information processed by said process means.

88. The system as recited in claim 87, wherein said weighing scale device further includes:
an input means for inputting user-input information.

89. The system as recited in claim 87, wherein said output means includes:
a display means, coupled to said process means, for displaying the diet information processed by said process means; and
a print means, coupled to said process means, for printing the diet information processed by said process means.

90. The system as recited in claim 89, wherein said display means includes a liquid crystal display (LCD).

91. The system as recited in claim 89, wherein said print means includes a printer.

92. The system as recited in claim 87, said weighing scale device further includes:
a second detection means for detecting a fingerprint of a user to identify the user at said weighing scale device.

93. The system as recited in claim 88, wherein the user-input information includes a user identity, a user sex, a height value, a target time period and a target weight value.

94. The system as recited in claim 93, wherein said information provision means includes:
a communication interface means for receiving the current weight value from said weighing scale device and transmitting the diet information to said weighing scale device;
a user identification means, coupled to said communication interface means, for identifying the user identity contained in the user-input information;
a first calculation means coupled to said user identification means, for calculation a difference between the current weight value and a previous weight value;
a second calculation means, coupled to said first calculation means, for calculating the number of calories required by the day on the basis of the difference, the number of calories consumed by the day and a user-body fat level; and
an information generation means coupled between said communication interface means and said second calculation means, for generating the diet information in response to the number of calories required by the day.

95. The system as recited in claim 94, wherein said storage means further stores the user-input information, the previous weight value, the number of calories consumed by the day and the user-body fat level.

96. The system as recited in claim 95, wherein the user-input information further includes the waist and hip circumference values.

97. The system as recited in claim 95, wherein the diet information includes the weight variation value, the today diet list and the recommended physical exercise information.

98. The system as recited in claim 95, wherein the weight variation value includes a weight increment and a weight decrement.

99. The system as recited in claim 88, wherein said common communication line is coupled to an Internet network.

100. The system as recited in claim 99, wherein said information provision means includes:
a server computer coupled to the Internet network, said server computer having a World-Wide Web (Web) site, which is made up of at least one Web page.

101. The system as recited in claim 100, further comprising:
a client computer coupled to the Web page over the Internet network.

102. The system as recited in claim 101, wherein the Web page contained in the Web site includes the user-input information received from said client computer.

103. The system as recited in claim 88, wherein said input means contained in said weighing scale device includes a keyboard.

104. The system as recited in claim 87, wherein said weighing means contained in said weighing scale device includes a weighing pad.

105. The system as recited in claim 86, wherein said circumference measuring means contained in said weighing scale device includes a measuring rope.

106. A method for outputting diet information, comprising the steps of:
a) weighing a current user body to detect a current weight value;
b) providing the diet information corresponding to the current weight value from a server computer to a weighing scale device by employing a database storing a weight variation value, today diet list and recommended physical exercise information;
c) outputting the diet information;
said step a) further includes the step of:
a1) measuring waist and hip circumferences;
a2) detecting waist and hip circumference values from the waist and hip circumferences measured; and
a3) transmitting the waist and hip circumference values from the weighing scale device to the server computer.

107. The method as recited in claim 106, wherein said step a) includes the steps of:
a4) weighing the current user body;
a5) detection the current weight value from the current user body weighed; and
a6) transmitting the current weight value from the weighing scale device to server computer.

108. The method as recited in claim 107, wherein said step
a) further includes the step of:
a7) inputting user-input information.

109. The method as recited in claim 106, wherein said step c) includes the steps of:
c1) receiving the diet information from the server computer;
c2) processing the diet information;
c3) displaying the processed diet information on a liquid crystal display (LCD); and
c4) printing the processed diet information.

110. The method as recited in claim 108, wherein the user-input information contained in said step a7) includes a user identity, a user sex, a height value, a target time period and a target weight value.

111. The method as recited in claim 110, wherein said step b) includes the steps of:
receiving the current weight value from the weighing scale device;
identifying the user identity contained in the user-input information;
calculation a difference between the current weight value and a previous weight value stored in a database;
calculating the number of calories required by the day on the basis of the difference, the number of calories consumed by the day and the user-body fat level stored in a database; and
generating the diet information to the weighing scale device.

112. The method as recited in claim 111, wherein said step b) further includes the step of:
storing the user-input information, the previous weight value, the weight variation value, the today diet list, the recommended physical exercise information, the number of calories consumed by the day and the body fat level.

113. The method as recited in claim 112, wherein the user-input information contained in said step of storing the user-input information further includes the waist and hip circumference values.

114. The method as recited in claim 112, wherein said diet information includes the weight variation value, the today diet list and the recommended physical exercise information.

115. The method as recited in claim 112, wherein the weight variation value includes a weight increment and a weight decrement.

116. A computer-readable medium storing program instructions, the program instructions disposed on a computer to perform a method for outputting diet information, the method comprising the steps of:
a) weighing a current user body to detect a current weight value;
b) providing the diet information corresponding to the current weight value from a server computer to a weighing scale device by employing a database storing a weight variation value, today diet list and recommended physical exercise information;
c) outputting the diet information;
wherein said step a) further includes the steps of:
a1) measuring waist and hip circumferences;
a2) detecting waist and hip circumference value from the waist and hip circumferences measured; and
a3) transmitting the waist and hip circumference values from the weighing scale device to the server computer.

117. The computer-readable medium as recited in claim 116, wherein said step a) includes the steps of:
a4) weighing the current user body;
a5) detecting the current weight value from the weighing scale device to the server computer.

118. The computer-readable medium as recited in claim 117, wherein said step a) further includes the step of:
   a6) inputting user-input information.

119. The computer-readable medium as recited in claim 116, wherein said step c) includes the steps of:
   c1) receiving the diet information from the server computer;
   c2) processing the diet information;
   c3) displaying the processed diet information on a liquid crystal display (LCD); and
   c4) printing the processed diet information.

120. The computer-readable medium as recited in claim 118, wherein the user-input information contained in said step a6) includes a user identity, a user sex, a height value, a target time period and a target weight value.

121. The computer-readable medium as recited in claim 120, wherein said step b) includes the steps of:
   receiving the current weight value from the weighing scale device;
   identifying the user identity contained in the user-input information;
   calculation a difference between the current weight value and a previous weight value;
   calculation the number of calories required by the day on the basis of the difference, the number of calories consumed by the day and a user-body fat level stored in a database;
   generation the diet information in response to the number of calories required by the day; and
   transmitting the diet information to the weighing scale device.

122. The computer-readable medium as recited in claim 121, wherein said step b) further includes the step of:
   storing the user-input information, the previous weight value, the weight variation value, the today diet list, the recommended physical exercise information, the number of calories consumed by the day and the body fat level.

123. The computer-readable medium as recited in claim 122, wherein the user-input information contained in said step of storing the user-input information further includes the waist and hip circumference values.

124. The computer-readable medium as recited in claim 121, wherein said diet information includes the weight variation value, the today diet list and the recommended physical exercise information.

125. The computer-readable medium as recited in claim 116, wherein the weight variation value obtained in the diet information includes a weight increment and a weight decrement.

* * * * *